United States Patent [19]

Swan et al.

[11] Patent Number: 5,414,075
[45] Date of Patent: May 9, 1995

[54] RESTRAINED MULTIFUNCTIONAL REAGENT FOR SURFACE MODIFICATION

[75] Inventors: Dale G. Swan, St. Louis Park; Charles A. Hastings, Hopkins, both of Minn.

[73] Assignee: BSI Corporation, Eden Prairie, Minn.

[21] Appl. No.: 972,533

[22] Filed: Nov. 6, 1992

[51] Int. Cl.$^6$ .................. C07C 49/00; C12N 11/00
[52] U.S. Cl. .................. 568/333; 568/332; 435/177; 435/180
[58] Field of Search .................. 427/447; 436/501; 435/177, 180, 182; 530/815, 816; 568/332, 333

[56] References Cited

U.S. PATENT DOCUMENTS

| | | | |
|---|---|---|---|
| 4,722,906 | 2/1988 | Guire | 436/501 |
| 4,973,493 | 11/1990 | Guire | 427/2 |
| 4,979,959 | 12/1990 | Guire | 623/66 |
| 5,002,582 | 3/1991 | Guire et al. | 623/66 |

FOREIGN PATENT DOCUMENTS 8905616 12/1988 WIPO .

OTHER PUBLICATIONS

Cazaux et al., Tetrahedron Letters 30:1369–1372 (1989) "A Barium Selective Macrocyclic Tetralactam . . . ".
Yamamoto et al., Tetrahedron Letters 27:49–50 (1986) "Restricted Internal Rotation . . ."
Kroschwitz, "Plastics", pp. 462–464, in *Concise Encyclopedia of Polymer Science and Engineering*, ed., John Wiley and Sons, 1990.
Jentoft, N. and D. G. Dearborn, *J. of Biol. Chem.* 254:4359 (1979).
Jemmerson, R., "Antigenicity and Native Structure of Globular Proteins: Low Frequency of Peptide Reactive Antibodies", *Proc. Nat. Acad. Sci. USA*, 84:9180, 1987.
Stevens, F. J., "Considerations of the Interpretation of the Specificity of Monoclonal Antibodies Determined in Solid-Phase Immunoassays," in *Immunochemistry of Solid-Phase Immunoassay*, J. E. Butler, ed., CRC Press, 233, 1991.
Jemmerson, R., "Multiple Overlappings Epitopes in the Three Antigenic Regions of Horse Cytochrome c," *J. Immunol.* 128:213, 1987.

Primary Examiner—Margaret Parr
Assistant Examiner—Eggerton Campbell
Attorney, Agent, or Firm—Fredrikson & Byron

[57] ABSTRACT

A multifunctional reagent is provided that is useful for the attachment of desired molecules to support surfaces. A reactive reagent molecule of the invention is "restrained" in that it is conformationally and/or chemically restricted from reacting with either itself or with other molecules of the same reagent. Upon activation, this feature causes the attachment of less than all of the reactive sites of the multifunctional reagent to a surface, thereby leaving the remaining sites free to react with molecules desired to be immobilized onto the surface.

20 Claims, No Drawings

RESTRAINED MULTIFUNCTIONAL REAGENT FOR SURFACE MODIFICATION

TECHNICAL FIELD

The present invention relates to chemical and/or physical modification of the surface properties of industrially and medically important substrates. In a further aspect, the present invention relates to the various processes useful for modifying the surface properties of bulk materials for specific applications. In this aspect, the present invention relates to such surface modification techniques as plasma deposition, radiation grafting, grafting by photopolymerization, ion implantation, and chemical derivatization.

BACKGROUND OF THE INVENTION

The chemical modification of surfaces, to achieve desired chemical and/or physical characteristics, has been previously described. U.S. Pat. Nos. 4,722,906; 4,973,493; 4,979,959; and 5,002,582 (the disclosures of each of which are incorporated herein by reference), for example, relate to surface modification by the use of latent reactive groups to achieve covalent coupling of reagents such as biomolecules and synthetic polymers to various substrates. The preferred latent reactive group is typically described as a photochemically reactive functional group (i.e., photoreactive group) that, when exposed to an appropriate energy source, undergoes a transformation from an inactive state (i.e., ground state) to a reactive intermediate capable of forming covalent bonds with appropriate materials.

Such latent reactive groups are typically described as being used to first derivatize a desired compound (e.g., thermochemically), followed by the application (photochemically) of the derivatized compound to a surface. Such a sequential approach is suitable in many situations, but the approach can lack such attributes as speed, versatility, and ease of use, such as for target molecules that are inherently difficult to first derivatize.

What would be clearly desired would be a reactive reagent that provides an optimal combination of the speed, versatility, and ease of use necessary for the derivatization of suitable surfaces, particularly one that is useful either simultaneously with the application of a target molecule, or one that can be used to prime a surface prior to the application of a target molecule.

SUMMARY OF THE INVENTION

We have discovered a novel restrained, multifunctional reagent useful for prior derivatization of a support surface, or for simultaneous application with a target molecule to a support, the reagent comprising a chemical backbone having attached to it one or more first latent reactive groups and one or more second latent reactive groups, each of the first and second latent reactive groups being attached to the backbone in such a manner that, upon activation of the latent reactive groups in the presence of a support surface,
  a) the first latent reactive groups are capable of covalently bonding to the support surface, and
  b) upon bonding of the first latent reactive groups to the surface, the second latent reactive groups are;
    i) restricted from reacting with either a spacer or the support surface,
    ii) capable of reverting to their inactive state, and
    iii) upon reverting to their inactive state, are thereafter capable of being reactivated in order to later bind a target molecule, thereby attaching the target molecule to the surface..

In a particularly preferred embodiment, the chemical backbone of such a nultifunctional reagent is a single tetrahedral carbon atom. Attached to the central carbon, in this embodiment, are four identical latent reactive groups, in the form of photoreactive groups, each attached via identical spacer chains. Upon exposure to a suitable light source, each of the latent reactive groups are subject to activation.

By virtue of conformational and/or steric constraints that the reagent imposes on itself (hence "restrained"), both by the tetrahedral nature of the central carbon, as well as the physical-chemical nature of the spacer chains themselves (e.g., their length, reactivity, and flexibility), the reagent is restricted, in that a maximum of three of the four activated latent reactive groups on any given preferred reagent molecule are able to attach to the support surface. The remaining unreacted group(s) are thus able to revert to their inactive state. One can visualize the resultant structure as being analogous to a four-pronged child's jack being tossed onto a table. Three of the prongs will rest on the surface of the table, with the fourth pointing up and away from the table.

In a subsequent step, the unreacted group(s) can be reactivated in the presence of a target molecule, in order to covalently bond the target molecule to the surface.

The reagent of the present invention has broad applicability, particularly since it can be used to provide a "primed" surface, i.e., a surface having latent reactivity for a target molecule. The reagent is therefore particularly useful in situations where the available quantity of the target molecule is limited; where prior derivatization of a target molecule would create an insoluble or inactive product; or where there is a desire to prepare and store a primed surface for later use, e.g., with a variety of target molecules.

The reagent can also be used to prepare a primed latent reactive surface for the subsequent application of a target molecule that has itself been previously derivatized with latent reactive groups, i.e., latent reactive groups provided by compounds other than what may be present in the respective restrained reagent. This approach could be useful for providing increased sites of bonding between the surface and the target molecule.

Additionally, the reagent provides a further benefit in that it can be used in a mixture with target molecules (nonderivatized or previously derivatized), in the presence of a surface, to permit simultaneous application (in contrast to the sequential application described above) in the course of surface modification.

DETAILED DESCRIPTION

The reagent of the present invention involves a chemical backbone having attached to it one or more first latent reactive groups capable of attaching to a surface, and one or more second latent reactive groups capable of attaching to a target molecule intended for immobilization. Chemically, the first and second latent reactive groups, and respective spacers, can be the same or different.

In situations in which all latent reactive groups and spacers are chemically, or at least functionally, the same, the distinction between first and second latent reactive groups may actually be accomplished at the time of the first activation step, i.e., those groups that are activated and attach to the surface will be considered "first" latent reactive groups, and those that remain unreacted (whether or not they have been activated) will be considered "second" latent reactive groups.

The first and second latent reactive groups are preferably attached to the backbone by spacer chains in such a manner that, upon activation of the latent reactive groups in the presence of a support surface, the first latent reactive groups are capable of covalently bonding to the surface. The second latent reactive groups are thereby conformationally restricted, thus preventing reaction with either their spacers, other restricted reagents of the same type, or the support surface. In addition, after the first activation step and removal of the activating stimulus (e.g., illumination source), the second latent reactive groups are capable of reverting to their inactive state and can thereafter be activated (or reactivated, as the case may be) to covalently bond a target molecule.

The following diagram depicts the concept of the preferred tetrahedral core structure, as exemplified by the empirical formula $X(Y)_4(Z)_4$, shown below as Formula I:

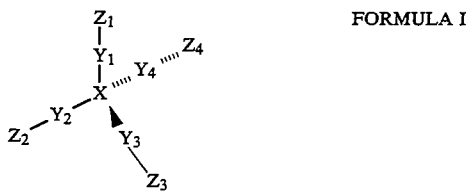

FORMULA I

In Formula I:

| | |
|---|---|
| X | = the chemical backbone; |
| $Y_1, Y_2, Y_3, Y_4$ | = optional spacers; and |
| $Z_1, Z_2, Z_3, Z_4$ | = latent reactive groups. |

As used herein, the term "chemical backbone" refers to the atom, or other molecular structure, to which either the latent reactive groups or spacers are attached, and which provides, at least in part, the desired steric and conformational restrictiveness between groups or spacers that are attached to the same chemical backbone. The term "core molecule" will be used to refer to the combination of chemical backbone and any attached spacers (i.e., "X+Y" in Formula I above), that is, without latent reactive groups.

The term "latent reactive group", as described more fully below, will refer to the activatible group attached to a spacer, that is used to bond with either the support surface ("first" latent reactive group) or the target molecule ("second" latent reactive group). The word "active" refers to a latent reactive group that has been subjected to an appropriate stimulus, in order to render it capable of forming a covalent bond with a suitable moiety. The word "inactive" refers to a latent reactive group either before activation, or after one or more cycles of activation and reversion to the inactive state. The term "target molecule", in turn, will be used to refer to the molecule that is intended to be attached to the surface, via the reagent, generally in order to provide the desired characteristics conveyed by virtue of its binding.

In a particularly preferred embodiment, the invention provides a core molecule containing four dimethyleneoxy groups ($-CH_2-O-CH_2-$) bonded as spacers to a central tetrahedral carbon atom, the carbon atom serving in this instance as the chemical backbone. The backbone, spacers, and latent reactive groups are described herein, for the sake of simplicity, as being distinct portions of the reagent of the present invention. In the chemical synthesis of a reagent however, these portions will rarely be provided as three independent precursors. Instead, and most often, the portion referred to herein as the spacer will be formed as the result of the reaction between two molecules, one that contains the core molecule and another that contains the latent reactive group.

By virtue of the physical and chemical properties of the photoreactive groups and the methylene group spacers, together with the conformational restrictions provided by the tetrahedral carbon backbone, the reagent is able to attach up to three of its photoreactive groups to a surface upon photoactivation. Being conformationally restricted, and thus unable to interact with the support surface or the spacers, any remaining photoreactive group(s) are able to return to their inactive states upon removal of light, once again being capable of activation by subsequent illumination.

In addition to reagents of the particularly preferred embodiment, containing a central carbon atom, reagents of the present invention can be prepared having any suitable chemical (e.g., organic and/or inorganic) backbone structure, including those that employ a single atom, such as silicon, nitrogen, phosphorus, and any other atom with four or more bonds nonplanar with respect to one another.

Also, molecules having conformationally restricted ring structures (such as inositol, i.e., hexahydroxy cyclohexane) can be derivatized with latent reactive groups in a manner analogous to that described herein for pentaerythritol, to provide latent reactive groups in both axial and equatorial positions. Other polyhydroxylated compounds such as mono- and di-saccharides, and cyclodextrins, are suitable as well, in that they offer alternative opportunities to create other multisubstituted reagents having varying placements and densities of latent reactive groups.

Contact with a support surface and activation of the latent reactive groups will result in covalent bond formation through at least one latent reactive group, with at least one other latent reactive group being conformationally restricted and thus unable to react at the surface.

Spacers useful in the reagent of the present invention can be bonded to the tetrahedral atom and can be of any suitable length and structure. A "spacer", as used herein, refers to that region of a reagent between a latent reactive group and a chemical backbone. The use of spacers is optional, and would not be necessary, for instance, for such compounds as acylated derivatives of tetraphenylmethane having the structure shown below as FORMULA II:

FORMULA II

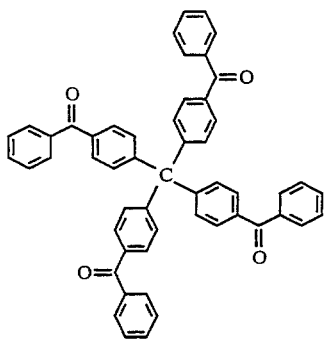

Functionally, it is particularly preferred that a spacer does not have any groups or atoms that would be both physically accessible to, and chemically reactive with, an activated latent reactive group (whether from the same or another reagent molecule), to an extent that would render the reagent useless for its intended purpose. At the very least, the spacer should have no atom or groups that would kinetically compete with the binding of latent reactive groups to their intended target, be it a surface or a target molecule. For instance, preferred spacers should typically not have any accessible "abstractable hydrogen" atoms, i.e., hydrogen atoms that are accessible to and reactive with the activated latent reactive group of choice.

Molecular modeling techniques, as are available to and within the skill of those in the art, can be used to determine the optimal length and structure of spacers needed to keep latent reactive groups conformationally restricted from reacting. Typically the spacer will have no linear region longer than about 5 atoms (i.e., 6 bonds), and preferably 4 atoms (5 bonds), in length. Although it is not required that the spacers within a particular reagent be chemically identical, the use of different spacers in a single reagent molecule is not generally preferred; in that such an embodiment will typically require more synthetic steps and may require more complex chemical separations in their preparation.

Constituent atoms of the spacers need not be aligned linearly. For example, aromatic rings, which lack abstractable hydrogen atoms (as defined above), can be included as part of spacer design in those reagents where the latent reactive group functions by initiating covalent bond formation via hydrogen atom abstraction. In its precursor form (i.e., prior to attachment of a latent reactive group), a spacer can be terminated with any suitable functionality, such as hydroxyl, amino, carboxyl, and sulfhydryl groups, which is suitable for use in attaching a latent reactive group by a suitable chemical reaction, e.g., conventional coupling chemistry.

A "latent reactive group", as used herein, refers to a chemical group that responds to an applied external energy source in order to undergo active specie generation, resulting in covalent bonding to an adjacent chemical structure (e.g., an abstractable hydrogen). Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive aryl ketones such as acetophenone and benzophenone, or their derivatives, are preferred, since these functional groups, typically, are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoreactive aryl ketones are particularly preferred.

The method of the present invention involves the attachment of a target molecule to a support surface by use of the above-described reagent,. As will be discussed more fully below, the reagent can be used in a number of different ways to achieve the desired result.

The method of the present invention comprises the steps of

A. Providing a multifunctional reagent comprising a chemical backbone having attached to it one or more first latent reactive groups and one or more second latent reactive groups, each of the first and second latent reactive groups being attached to the backbone in such a manner that upon activation of the latent reactive groups in the presence of a support surface,
 (1) the first latent reactive groups are capable of covalently bonding to the surface, and
 (2) upon bonding of the first latent reactive groups to the surface, the second latent reactive groups are
  a. conformationally restricted from reacting with either a spacer or the support surface,
  b. capable of reverting to their inactive state, and
  c. upon reverting to their inactive state, capable of being reactivated in order to later bind a target molecule in order to attach the target molecule to the surface, B. activating the first latent reactive groups in the presence of the support surface, in order to bond the first latent reactive groups to the surface, and C. activating the second latent reactive groups in the presence of the target molecules, in order to bond the second latent reactive groups to the target molecules, thereby attaching the target molecules to the surface.

The steps of the method can be performed in arty suitable order. For example, a multifunctional reagent as described above can physically absorb itself to a suitable support surface by hydrophobic interactions. Upon illumination, the photoreactive groups (e.g., benzophenone groups) undergo covalent bond formation at the support surface by the aforementioned mechanism. Given the conformational restrictions of the tetrahedral bonding core atom, at least one, and up to three of the four photoreactive groups form bonds with the surface. With the absence of abstractable hydrogens in the proximity of the remaining unbonded photoreactive group(s), and removal of the illumination source, the excited state benzophenone returns to ground state energy. These remaining groups are then capable of being reactivated when the target molecule intended for immobilization is present and when the treated surface is exposed to another round of illumination. This method can be described as a "two-step" approach, where the photoreactive reagent is applied in the first step to create the latent reactive surface, and in the second step, the target molecule is added for attachment to the activated surface.

In another embodiment, which can be described as a "one-step" method, the reagent of the present invention is mixed in solution with the target molecule to form a binary composition, and this composition is used to surface modify materials in a single illumination step. In this case, illumination triggers not only covalent bond formation of the latent reactive group with the material surface, but also simultaneously triggers covalent bond formation with adjacent target molecules residing on the surface. In the course of this process, however, the reagent is substantially precluded from bonding to other reagent molecules by virtue of conformational restrictions and/or the lack of abstractable hydrogen atoms.

In yet another embodiment, the invention provides a method of using a multifunctional reagent to pretreat a substrate surface prior to the application and bonding of molecules that have themselves been functionalized with latent reactive groups. This method is useful in situations where a particularly difficult substrate requires maximal coating durability. In this manner, the number of covalent bonds formed between the substrate surface and the target molecule derivatized with latent reactive groups can typically be increased, as compared to surface modification with a desired latent reactive group-containing target molecule alone. This approach offers significant advantages, e.g, in terms of increasing the tenacity of binding of the desired molecule to the surface, without having to increase the latent reactive group content of the target molecule to a point where properties such as the solubility or functional activity of the molecule would be impaired.

In view of the present disclosure, reagents of the present invention can be prepared according to conventional synthetic methods. A preferred reagent, for instance, can be prepared according to the following protocol: A mixture of the core molecule (e.g., pentaerythritol) and an excess of a derivative of the latent reactive group (e.g., 4-bromomethylbenzophenone) are dissolved in a suitable solvent and refluxed in the presence of a base capable of alkoxide anion generation. The product, a tetrakis (4-benzoylbenzyl ether) of pentaerythritol can then be purified by preparative chromatography. The product has the structure shown below as FORMULA III:

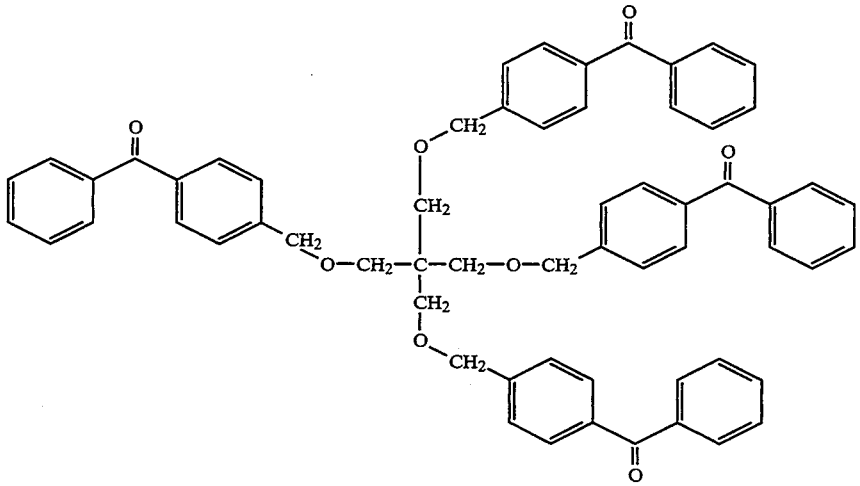

FORMULA III

Any suitable coupling chemistry can be used to attach the latent reactive group to the core molecule. For example, an ester coupling group can be prepared by reaction of 4-benzoylbenzoyl chloride with pentaerythritol, using a suitable solvent and acid scavenger. Similarly, a urethane coupling group can be generated by reaction of 4-benzophenone isocyanate with pentaerythritol. Also, where the tetrahedral core molecule contains spacers terminated with amine functional groups, as opposed for instance to hydroxyl groups, a latent reactive group can be introduced via an amide functionality, using an acid chloride or an N-oxysuccinimide ester.

Likewise, if the core molecule spacers are terminated with sulfhydryl groups, a maleimide-substituted latent reactive group can be used in the coupling reaction. The coupling reaction of the core molecule (such as pentaerythritol) with the latent reactive group can be preceded by the synthesis of a core molecule that includes not only the pentaerythritol precursor but also spacer extensions based on molecules that are nonreactive or sterically hindered with respect to reaction with the latent reactive group.

Reagents of the present invention can be used to modify any suitable surface. Where the latent reactive group of the reagent is a photoreactive group of the preferred type, it is particularly preferred that the surface provide abstractable hydrogen atoms suitable for covalent bonding with the activated group.

Plastics such as polyolefins, polystyrenes, poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, cellulose derivatives, silicones, and rubber-like plastics can all be used as supports, providing surfaces that can be modified as described herein. See generally, "Plastics", pp. 462–464, in *Concise Encyclopedia of Polymer Science and Engineering*, Kroschwitz, ed., John Wiley and Sons, 1990, the disclosure of which is incorporated herein by reference. In addition, supports such as those formed of pyrolytic carbon and silylated materials such as glass ceramic, or metal are suitable for surface modification.

Suitable target molecules for use in the present invention, for attachment to a support surface, encompass a diverse group of substances. Target molecules can be used in either an underivatized form, or previously derivatized. Moreover, target molecules can be immobilized singly or in combination with other types of target molecules. In addition, target molecules can be immobilized to the surface either after (e.g., sequentially), or during (e.g., simultaneously with) attachment of the present multifunctional reagent to the surface.

Typically, target molecules are selected so as to confer particular desired properties to the surface and/or to the device or article bearing the surface. Examples of suitable target molecules, and the surface properties they are typically used to provide, is represented by the following non-limiting list:

| TARGET MOLECULE | FUNCTIONAL ACTIVITY |
|---|---|
| Synthetic Polymers | |
| Sulfonic acid-substituted polyacrylamide | Lubricity, negatively charged surface, hydrophilicity |
| Polyacrylamide | Lubricity, protein repulsion, hydrophilicity |
| Polyethylene glycol | Lubricity, cell and protein repulsion, hydrophilicity |
| Polyethyleneimine | Positively charged surface |
| Polylactic acid | Bioerodible surface |
| Polyvinyl alcohol | Lubricity, hydrophilicity |
| Polyvinyl pyrrolidone | Lubricity, hydrophilicity |
| Quaternary amine-substituted polyacrylamide | Lubricity, positively charged surface |
| Silicone | Lubricity, hydrophobicity |
| Conductive polymers (e.g., polyvinylpyridine, polyacetylene, polypyrrole) | Electric conductivity |
| Carbohydrates | |
| Alginic acid | Lubricity, hydrophilicity |
| Cellulose | Lubricity, hydrophilicity, biodegradable glucose source |
| Chitosan | Positively charged surface, hydrophilicity |
| Glycogen | Hydrophilicity, biodegradable glucose source |
| Heparin | Antithrombogenicity, hydrophilicity, cell attachment |
| Hyaluronic acid | Lubricity, negatively charged surface |
| Pectin | Lubricity, hydrophilicity |
| Mono-, di- saccharides | Hydrophilicity |
| Dextran sulfate | Chromatography media |
| Proteins | |
| Antibodies | Antigen binding |
| Antithrombotic agents (e.g., antithrombin III) | Antithrombogenic surface |
| Albumin | Nonthrombogenic surface |
| Attachment proteins/peptides (e.g. collagen) | Cell attachment |
| Enzymes | Catalytic surfaces |
| Extracellular matrix proteins/peptides | Cell attachment and growth |
| Growth factors, proteins/peptides | Cell growth |
| Hirudin | Antithrombogenic surface |
| Thrombolytic proteins (e.g., streptokinase, plasmin, urokinase) | Thrombolytic activity |
| Lipids | |
| Fatty acids | Hydrophobicity, biocompatibility |
| Mono-, di- and triglycerides | Hydrophobicity, lubricity, biodegradable fatty acid source |
| Phospholipids | Hydrophobicity, lubricity, biodegradable fatty acid source |
| Prostaglandins/leukotrienes | Nonthrombogenic surface/immobilized messengers |

| TARGET MOLECULE | FUNCTIONAL ACTIVITY |
|---|---|
| Nucleic Acids | |
| DNA | Substrate for nucleases/affinity binding |
| RNA | Substrate for nucleases/affinity binding |
| Nucleosides, nucleotides | Source of purines, pyrimidines, enzyme cofactors |
| Drugs/vitamins/cofactors | |
| Enzyme cofactors | Immobilized enzymes |
| Heme compounds | Globin bindings/surface oxygenation |
| Drugs | Drug activity |
| Non-polymeric Materials | |
| Dyes (e.g., azo dyestuffs) | Coloring agents |
| Fluorescent compounds (e.g., fluorescein) | Fluorescence |

Any suitable technique can be used for reagent attachment to a surface, and such techniques can be selected and optimized for each material, process, or device. The multifunctional reagent has been successfully applied to clean material surfaces as listed above by spray, dip, or brush coating of a solution of the reactive reagent. In a typical application, the support intended for coating is first dipped in a solution of the reagent diluted with a suitable solvent (e.g., isopropyl alcohol). The reagent-coated support is then exposed to ultraviolet light in order to promote covalent bond formation at the material surface. After washing to remove any unbound reagent, application of the molecule intended for immobilization, followed by a second UV illumination, results in surface modification with the target molecule.

When desired, other approaches can be used for surface modification using the reagent of the present invention. For example, the latent reactive reagent can be mixed directly with the molecule intended for immobilization. The tetrakis (4-benzoylbenzyl ether) of pentaerythritol at 0.1 mg/ml when mixed with nitrocellulose at 40 mg/ml can be used to surface modify polyvinylidene difluoride membranes with a single illumination step. In another experimental approach, the photoreactive derivatives of these synthetic and naturally occurring molecules can also be applied to surfaces pretreated with multifunctional reagents such as the tetrakis (4-benzoylbenzyl ether) of pentaerythritol. This approach is particularly useful in those situations in which a support is difficult to modify using conventional chemistry, or for situations that require exceptional durability and stability of the target molecule on the surface.

The present invention provides a reagent and method useful for altering the surface properties of a variety of devices of medical, scientific, and industrial importance, using a broad spectrum of suitable target molecules.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments.

EXAMPLES

EXAMPLE 1

Preparation of Tetrakis (4-benzoylbenzyl ether) of Pentaerythritol ["tetra-BBE-PET"]

Pentaerythritol [Aldrich] (2.0 g; 14.71 mmole; dried at 60° C. at <1 mm Hg for 1 hour), 4-bromomethylbenzophenone (20.0 g; 72.7 mmole; prepared by free radical bromination of 4-methylbenzophenone [Aldrich]), 80% (w/w) sodium hydride in mineral oil [Aldrich] (NaH 1.23 g; 41.0 mmole), and tetrahydrofuran ("THF", 120 ml) were refluxed for 34 hours in an argon atmosphere. An additional amount of 80% NaH (2.95 g; 98.3 mmole) was then added to the reaction mixture, and the mixture refluxed for an additional 7 hours under argon. The reaction was quenched by the addition of 8 ml of glacial acetic acid (HOAc). The quenched reaction was centrifuged to aid in the removal of THF insolubles.

The liquid was decanted, and the insolubles were washed with three 50 ml portions of chloroform ($CHCl_3$). The decanted liquid (mainly THF) and the $CHCl_3$ washes were combined and evaporated to give 18.7 g of a crude yellow semi-solid residue. A portion of the crude product (2 g) was purified by flash chromatography, using a 40 mm (1.58 in.) diameter×200 mm (8 in.) long silica gel column eluted with $CHCl_3$ and diethyl ether ($Et_2O$) according to the following table (unless otherwise indicated, all ratios are v/v):

| Solvent -(v/v) | | Solvent volume (ml) | Fraction numbers |
| --- | --- | --- | --- |
| $CHCl_3$ | 100 | 500 | 01-22 |
| $CHCl_3/Et_2O$ | 98/2 | 500 | 23-46 |
| $CHCl_3/Et_2O$ | 95/5 | 1000 | 47-93 |
| $CHCl_3/Et_2O$ | 90/10 | 500 | 94-118 |

A light yellow oily product (0.843 g; 59% theoretical yield) was obtained by combining and evaporating fractions 81–105 (In theory, a yield of 1.43 g tetra-BBE-PET would be expected from 2.0 g of the crude product placed on the column). The purified light yellow product was confirmed by analysis using a Beckman Acculab 2 infrared ("IR") spectrometer and a Varian FT-80 NMR spectrometer. The absence of a peak at 3500 cm-1 indicated the absence of hydroxyl functionality. Nuclear magnetic resonance analysis ($^1H$ NMR ($CDCl_3$)) was consistent with the desired product; aliphatic methylenes δ 3.6 (s, 8 H), benzylic methylenes δ 8 4.5 (s, 8 H), and aromatics δ 7.15–7.65 (m, 36 H) versus tetramethylsilane internal standard.

It is clear, therefore, that a reagent can be prepared having the desired physical and chemical characteristics embodied in this invention. The reagent was used to couple various target molecules to support surfaces as described in EXAMPLES 3 through 13.

EXAMPLE 2

Preparation of Tetrakis (4-benzoylbenzoate ester) of Pentaerythritol [tetra-BBA-PET]

Pentaerythritol [Aldrich] (136 mg; 1 mmole), 4-benzoylbenzoyl chloride (1.0 g; 4.09 mmole; prepared by the reaction of thionyl chloride and 4-benzoylbenzoic acid [Aldrich]), triethylamine [Aldrich] (696 ml; 5 mmole), and chloroform (10 ml) were stirred overnight at room temperature. The reaction mixture was placed in ice cold hydrochloric acid (0.5M; 11 ml) and thoroughly mixed for 1 minute. The chloroform layer was separated, dried over sodium sulfate, and evaporated, yielding an orange residue (1.13 g). The residue was purified by flash chromatography using a 40 mm (1.57 in.) diameter by 180 mm (7 in.) long silica gel column, which was eluted with chloroform/acetonitrile, 96:4 (v/v). Seventy-two 13 ml fractions were collected. Fractions 37 to 61 were combined and evaporated to give a white solid (322 mg; 33% of theory). Analysis on a Varian FT-80 NMR spectrometer was consistent with the desired product: $^1H$ NMR ($CDCl_3$); aliphatic methylenes δ 5 4.7 (s, 8H) and aromatics δ 7.15–8.10 (m, 36H) versus tetramethylsilane internal standard.

Thus, it can be seen that a restrained multifunctional reagent can be prepared having ester groups as linkages. The reagent was used to modify polymethylmethacrylate (PMMA) for application of polyvinylpyrrolidone (PVP) as demonstrated in EXAMPLE 14.

EXAMPLE 3

Surface Modification of Polymethylmethacrylate (PMMA) by Sequential Application of tetra-BBE-PET and Polyvinylpyrrolidone (PVP)

A clear PMMA "coupon" (Rohm & Haas), 4 cm (1.57 in.)×2 cm (0.78 in.)×2 mm (0.08 in.), was first wiped with an isopropyl alcohol (IPA) soaked tissue, after which one-half of the coupon was brush coated with a 0.1 mg/ml solution of tetra-BBE-PET in IPA. After the coating had air-dried for 5 minutes under ambient conditions, the entire coupon was illuminated for 30 seconds, at a distance of 150 mm (6 in.) from a 100 watt short arc mercury vapor bulb. After a rinse with excess IPA to remove any unbound tetra-BBE-PET, the entire coupon was then brush coated with a 10 mg/ml solution of PVP (160,000 molecular weight; GAF Chemical Corp.) in deionized (DI) water. After the PVP had air-dried (approx. 5 min.), the coupon was again illuminated for 30 seconds in front of the same light source. The coupon was then rubbed extensively (approx. 1 min.) under a flow of DI water to check the durability of the PVP coating.

After this rinse, the half of the coupon that was coated with tetra-BBE-PET remained noticeably more wettable and lubricious to the touch than the half coated with PVP alone. The presence of the bound PVP on the tetra-BBE-PET coated half was verified by staining with a 0.35% solution of Congo Red (Sigma) in DI water.

EXAMPLE 4

Surface Modification of Polyethylene (PE) Tubing by Sequential Application of tetra-BBE-PET and a Mixture of Photo-derivatized Polymers (1:1)

Pieces of PE tubing (25 cm (9.8 in.))×(1.0 mm outer diameter (0.04 in.)) were first dip coated using a 0.1 mg/ml solution of tetra-BBE-PET in IPA. After the coating had air-dried (approx. 5 min.), the tetra-BBE-PET coated tubing was illuminated for 3 minutes midway between two opposed ELC-4000 lamps containing 400 watt metal halide/mercury vapor bulbs separated by a distance of 91 cm (36 in.). After a rinse with excess IPA to remove any unbound tetra-BBE-PET, the tubing was then dipped and subsequently withdrawn at a rate of 1.5 cm (0.59 in.)/sec from a solution containing 15 mg/ml photopoly [(acrylamide)-co-(2-acrylamido-2-methylpropanesulfonic acid)] ("photo-PA-AMPS ") and 15 mg/ml "photo-PVP" in water.

The photo-PA-AMPS was prepared by a copolymerization of acrylamide, 2-acrylamide-2-methylpropanesulfonic acid ("AMPS"), and N-(3-aminopropyl)methacrylamide ("APMA"), followed by photoderivatization of the polymer using 4-benzoylbenzoyl chloride under Schotten-Baumann conditions. The photo-PVP was prepared by copolymerization of 1-vinyl-2-pyrrolidone and APMA, followed by photoderivatization as described above. After the coating solution had dried (approx. 5 minutes at 55° C. (151 ° F.)), the tubing was again illuminated for 3 minutes.

Tubes coated with photo-PVP and photo-PA-AMPS alone have been shown to exhibit microscopic cracks, which can lead to flaking of the coating. In contrast, the tubes that were first coated with tetra-BBE-PET, and then coated with photo-PVP and photo-PA-AMPS, in the manner described above, showed little or no cracking.

EXAMPLE 5

Surface Modification of PE Tubing by Sequential Application of tetra-BBE-PET and a Mixture of Photo-PA-AMPS and Photo-PVP (2:1) (Wet illumination)

Pieces of PE tubing (25 cm, 9.8 in.)×(1.0 mm, O.D.,0.04 in.) were first dip coated with tetra-BBE-PET using a 0.1 mg/ml solution of the reagent in IPA. The tetra-BBE-PET coated tubing was immediately illuminated until dry (approx. 3 minutes) midway between metal halide/mercury vapor bulbs in the manner described in EXAMPLE 4. After a rinse with excess IPA to remove any unbound tetra-BBE-PET, the tubing was then immersed in a solution containing 10 mg/ml photo-PA-AMPS and 5 mg/ml of photo-PVP in 15% aqueous IPA, prepared in the manner described in Example 4, and then withdrawn at a rate of 1 cm (0.39 in.)/sec. The tubing was again illuminated until dry (approx. 3 minutes).

Tubes first coated with tetra-BBE-PET followed by photo-PVP and photo-PA-AMPS showed little or no cracking when evaluated by light microscopy, in contrast to previous experience with tubes similarly coated although lacking tetra-BBE-PET.

EXAMPLE 6

Surface Modification of Silicone Tubing by Sequential Application of tetra-BBE-PET and a Mixture of Photo-PA-AMPS and Photo-PVP (2:1) (Wet Illumination)

Pieces of silicone tubing (38 cm, 15 in.)×(5 mm, O.D, 0.20 in.) (Dow Coming) were first dip coated using a 0.1 mg/ml solution of tetra-BBE-PET in IPA. The tetra-BBE-PET coated tubing was immediately illuminated until dry (approx. 3 minutes) midway between two opposed Dymax PC-2 lamps containing 400 watt metal halide/mercury vapor bulbs, 51 cm (20 in.) apart. After a rinse with IPA to remove any unbound tetra-BBE-PET, the tubing was then immersed into a solution containing 10 mg/ml of photo-PA-AMPS and 5 mg/ml of photo-PVP in 15% aqueous IPA, prepared in the manner described in Example 4, and then withdrawn at a rate of 1 cm (0.39 in.)/sec. The tubing was again illuminated until dry (approx. 3 minutes).

Extensive washing and rubbing of the surface with fingers indicated a strongly adherent layer of the lubricious photo-PA-AMPS/photo-PVP. The presence of the bound PVP on the surface was also verified by staining with a 0.35% solution of Congo Red in DI water.

The Congo Red stain on silicone tubing that was coated with only photo-PVP and photo-PA-AMPS appeared spotty, indicative of areas where the coating was not bound to the surface and had therefore been rubbed off. However, robes that were first coated with tetra-BBE-PET and then coated with photo-PVP and photo-PA-AMPS appeared smoother and more contiguous, indicating that the tetra-BBE-PET was useful in increasing the tenacity and continuity of the PVP and PA coating.

EXAMPLE 7

Immobilization of PVP onto Polyvinylidene Difluoride (PVDF) Membranes Using tetra-BBE-PET PVDF membranes, which are normally quite hydrophobic, were rendered hydrophilic by the treatment of the membranes with tetra-BBE-PET, followed by subsequent exposure to unmodified PVP.

PVDF Immobilon TM -P Transfer Membranes (Millipore) were soaked for thirty minutes in a solution of 0.2 mg/ml of tetra-BBE-PET in MeOH. The membranes were removed from the tetra-BBE-PET solution and air-dried for five minutes. The membranes were suspended midway between opposed Dymax PC-2 lamps (51 cm (20 in.) apart) and illuminated for two minutes. The Dymax lamps contained 400 watt metal halide/mercury vapor bulbs. The membranes were washed three times with 100 ml of MeOH to remove unbound tetra-BBE-PET. After the final wash, the membranes were allowed to air-dry for five minutes.

The tetra-BBE-PET primed membranes were soaked for thirty minutes in PVP (Sigma, average MW of 360,000) solutions of varying concentration, (0 to 40 mg/ml) in MeOH. The membranes were removed from the PVP solutions and allowed to air-dry for five minutes. The membranes were suspended midway between opposed Dymax lamps 51 cm (20 in.) apart and illuminated for two minutes as described above. The membranes were washed for thirty minutes in 100 ml of MeOH with agitation. The MeOH wash was discarded and the washing procedure repeated three times. After the final wash, the membranes were removed and air-dried for five minutes.

The hydrophilicity of the PVDF membranes was evaluated by dropping membranes into a beaker filled with DI water and assessing their ability to absorb water. PVDF membranes that were treated with tetra-BBE-PET and exposed to 10 mg/ml PVP or greater, absorbed water instantaneously when placed in a beaker filled with water. They became translucent and sank to the bottom of the beaker. Untreated PVDF membranes were completely non-absorbent when placed in a beaker of water; they remained opaque and floated on the surface of the water indefinitely.

EXAMPLE 8

Immobilization of Nitrocellulose on PVDF Membrane Using tetra-BBE-PET

The incorporation of nitrocellulose (Hercules) onto PVDF membranes was accomplished by treatment of the membranes with tetra-BBE-PET followed by a subsequent exposure to unmodified nitrocellulose.

PVDF Immobilon TM -P Transfer Membranes (Millipore) were soaked for thirty minutes in a 0.2 mg/ml solution of tetra-BBE-PET in MeOH. The membranes were removed from the tetra-BBE-PET solution and air-dried for 5 minutes. The membranes were suspended midway between opposed Dymax lamps, 51 cm (20 in.) apart, and illuminated for two minutes. The Dymax lamps incorporated the same bulb as described in EXAMPLE 7. The membranes were washed three times with 100 ml MeOH to remove unbound tetra-BBE-PET. After the final wash, the membranes were air-dried for five minutes.

The tetra-BBE-PET primed membranes were soaked for thirty minutes in a 40 mg/ml nitrocellulose solution. The nitrocellulose used was Type RS grade 18-25, having a viscosity of 24 cps. The membranes were removed from the nitrocellulose solution and air-dried for five minutes. The membranes were suspended between Dymax lamps and illuminated for two minutes as described above. The membranes were washed with agitation for thirty minutes in 100 ml of MeOH. The MeOH wash was discarded and the washing procedure repeated three times. After the final wash the membranes were removed and allowed to air-dry for five minutes.

The protein binding characteristics of the primed membranes was compared to those of native nitrocellulose (Schleicher - Schuell) and unprimed PVDF membranes by a simple dot-blot binding assay (adapted from Easy-Titer ELIFA Septum Instructions, Pierce).

Bovine serum albumin CBSA", M.W.=66,000 Daltons) was dissolved in phosphate buffered saline (PBS) and serially diluted. Ten microliters of each dilution was pipetted into wells of the dot-blot manifold in duplicate. A vacuum was applied to the manifold to yield a flow rate of 14 ml/min. The presence of protein was determined with an enhanced colloidal gold stain. (Collodial Gold Total Protein Stain - Catalog No. 170-6527 and Gold Enhancement Kit - Catalog No. 170-6538, Bio-Rad).

Although all membranes tested detected 16 ng of protein (the limit of the assay), the signals generated on the hybrid membranes, as evaluated by visual inspection, were more intense than those on either nitrocellulose or unmodified PVDF membranes. This suggests that the hybrid membranes can provide a more sensitive assay matrix. Furthermore, the generation of stronger signals allows for a more definitive evaluation of protein binding. The results showed 16 ng of protein on the hybrid membranes gave a signal equivalent in intensity to approximately 125 ng of protein on nitrocellulose. Unmodified PVDF gave an equivalent signal at 63 ng of protein.

Using a low molecular weight protein (aprotinin, MW=6,500 D), the hybrid membrane was as sensitive as nitrocellulose. Both detected 400 ng of protein with approximately equivalent intensity of signal. In contrast, the limit of sensitivity of PVDF was only 1.6 µg. In addition, the intensity of the signal generated by the 1.6 µg on PVDF was markedly lower than that on the hybrid membrane (approximately equivalent to the signal generated by 400 ng on the hybrid membrane).

EXAMPLE 9

Co-Immobilization of Nitrocellulose on PVDF Membrane Using tetra-BBE-PET

A coating solution was prepared by dissolving nitrocellulose (Type RS grade 18-25 having a viscosity of 24 cps, Hercules Inc.) at 40 mg/ml and tetra-BBE-PET at 0.1 mg/ml in MeOH. PVDF Immobilon TM -P transfer membranes (Millipore) were soaked in the coating solution for thirty minutes. The membranes were removed and immediately suspended midway between opposed Dymax lamps, 51 cm (20 in.) apart, and illuminated for two minutes. The Dymax lamps used were of the same specifications as previously mentioned (EXAMPLE 7). The membranes were washed three times with 100 ml MeOH with agitation. After the final wash the membranes were air-dried for five minutes.

A coating could be seen upon visual inspection of the membranes. The protein binding characteristics of the hybrid membranes were compared to those of native nitrocellulose and PVDF membranes by a simple dot-blot binding assay (adapted from Easy-Titer ELIFA Septum Instructions, Pierce).

BSA (MW=66,000 Daltons) was dissolved in PBS and serially diluted. Ten microliters of each dilution was pipetted into wells of the dot-blot manifold in duplicate. A vacuum was applied to the manifold to yield a flow rate of 14 ml/min. The presence of protein was determined with an enhanced colloidal gold stain. (Collodial Gold Total Protein Stain - Catalog No. 170-6527 and Gold Enhancement Kit- Catalog No. 170-6538, Bio-Rad).

Similarly, all membranes tested detected 16 ng of protein (the limit of the assay) and the signals generated on the hybrid membranes were more intense, as evaluated by visual inspection, than those on either nitrocellulose or unmodified PVDF. Again this suggests that the hybrid membranes can provide a more sensitive assay matrix. Furthermore, the generation of stronger signals allows for a more definitive evaluation of protein binding. The results demonstrated that the signal of 16 ng of protein on the hybrid was more intense than the signal generated by 16 ng on PVDF but not as intense as that generated by 31 ng on PVDF. The intensity of the signal generated by 16 ng of protein on the hybrid membrane was approximately equivalent to that of 63 ng on nitrocellulose.

Again using a low molecular weight protein (aprotinin, MW=6,500 D), the hybrid membrane was as sensitive as nitrocellulose. Both detected 400 ng of protein with approximately equivalent intensity of signal. The limit of sensitivity of PVDF was only 1.6 µg. In addition, the intensity of the signal generated by 1.6 µg on PVDF was markedly lower than that on the hybrid membrane (approximately equivalent to the signal generated by 400 ng on the hybrid membrane).

EXAMPLE 10

Immobilization of Human Gamma Globulin (HGG) onto Microtiter Plates Using tetra-BBE-PET The covalent immobilization of HGG onto polystyrene microtiter plates was accomplished by pretreatment of the plates with tetra-BBE-PET followed by a subsequent exposure to an HGG solution.

Ninety-six well breakable polystyrene microtiter plates (Labsystems Inc.) were prewashed using 200 µls MeOH per well. Solutions of tetra-BBE-PET were prepared in MeOH with concentrations ranging from 0 to 0.5 mg/ml. The microtiter plates were divided into sections with each section receiving a different concentration of tetra-BBE-PET. One hundred microliters of solution was pipetted into each well. The solutions were incubated in the plates for one hour at room temperature. After incubating, the tetra-BBE-PET solutions were removed from the plates by aspiration. The plates were air-dried for thirty minutes. The plates were placed 48 cm (19 in.) beneath an ELC-4000 lamp and illuminated for two minutes. The ELC lamp uses a 400 watt metal halide/mercury vapor bulb. The plates were washed with 200 μl MeOH per well three times to remove unbound tetra-BBE-PET. The plates were air-dried for thirty minutes.

The tetra-BBE-PET activated plates were subsequently exposed to solutions of [$^3$H]-HGG in PBS Ph 7.2. Tritiated HGG was prepared by the reductive methylation of HGG with NaB[$^3$H]$_4$ and formaldehyde (Jentoft, N. and D. G. Dearborn, *J. of Biol. Chem.* 254:4359 (1979). The solutions of [$^3$H]-HGG ranged in concentration from 0 to 20 mg/ml. One hundred microtiters of the [$^3$H]-HGG solutions were added to each well. The solutions were incubated in the plates for 15 minutes at room temperature. The plates were placed 48 cm (19 in.) beneath an ELC lamp and illuminated for four minutes. The solutions were aspirated from the plates and the plates washed six times with 200 μl of PBS containing 0.05% TWEEN 20 per well.

The plates were broken apart and each well dissolved in two ml of tetrahydrofuran (THF). After dissolution of the wells was complete, 5 ml of liquid scintillation cocktail (Aquasol-2, Dupont) was added to each vial and the vials read on a liquid scintillation analyzer (Packard 1900 Calif.). From the total radioactivity found in each vial, the amount of [$^3$H]-HGG bound to each well can be calculated. The wells pre-treated with tetra-BBE-PET showed significantly greater amounts of [$^3$H]-HGG bound than did the untreated wells. This was particularly true at the higher concentrations of protein. Using an [$^3$H]-HGG concentration of 20 mg/ml, the tetra-BBE-PET pre-treated wells showed [$^3$H]-HGG binding increases of 37%, 52% and 56% over untreated wells at tetra-BBE-PET concentration of 0.1, 0.2 and 0.5 mg/ml respectively.

EXAMPLE 11

Surface Modification of Polystyrene with Sequential Application of teta-BBE-PET and Collagen Type IV

| Group | Treatment |
|---|---|
| 1 | tetra-BBE-PET, aspirated & dried, illuminated, rinsed, [$^3$H]collagen IV, aspirated & dried, illuminated. |
| 2 | tetra-BBE-PET, aspirated & dried, [$^3$H]collagen IV, aspirated & dried, illuminated. |
| 3 | Illuminated surface, adsorbed [$^3$H]collagen IV, aspirated & dried. |
| 4 | Adsorbed [$^3$H]collagen IV, aspirated & dried. |
| 5 | Adsorbed [$^3$H]collagen IV, aspirated & dried, illuminated. |
| 6 | Photo[$^3$H]collgen IV, aspirated & dried, illuminated. |

Polystyrene wells from a 96-well polystyrene breakaway plate (Dynatech Immulon I, inner diameter of 8.71 mm (0.343 inches) were coated with tetra-BBE-PET at 0.1 mg/ml in methanol (Groups 1 and 2). All wells were covered with Parafilm ® (American Can Company, Greenwich, Conn.) to prevent evaporation and were incubated for 1 hour at room temperature. After incubation, the tetra-BBE-PET solution was aspirated from the wells and the wells were air-dried for 5 minutes.

Wells from Group 1 were illuminated for 90 seconds, 20 cm (8 inches) from a Dymax PC-2 lamp. The Dymax lamp used contained a 400 watt metal halide/mercury vapor bulb. Wells in Group 2 were not illuminated at this point. The wells from Group 1 were rinsed 3 times with methanol. Another set of uncoated polystyrene wells (Group 3) were illuminated as described above. [$^3$H]Collagen IV, prepared from collagen IV (Sigma C-7521) by reductive methylation with NaB[$^3$H]$_4$ and formaldehyde (see Jentoft and Dearborn, above), was diluted to 0.1 mg/ml in PBS and added to the wells of Groups 1,2,3,4, and 5.

Photoderivatized [$^3$H]collagen IV, prepared from collagen IV (Sigma C-7521) by reductive,methylation (see Example 10), followed by photoderivatization using a process described in Example 1–3B of U.S. Pat. No. 4,973,493, was diluted to 0.1 mg/ml in PBS and added to the wells of Group 6. All wells were covered with parafilm to prevent evaporation and were incubated for 1 hour at room temperature. After incubation, the reagents were aspirated from the wells and the wells were air-dried for 10 minutes. Groups 1,2,4,5 and 6 were illuminated for 90 seconds as described above.

All groups underwent three 1 hour washes, an overnight wash in 1% Tween 20/PBS, followed by three 1 hour rinses in PBS. In preparation for scintillation counting, each well was dissolved in THF and mixed with scintillation cocktail. Finally, the number of disintegrations per minutes (DPM's) produced by each sample was measured using a Packard 1900CA Tri-Carb Liquid Scintillation Analyzer. The number of DPMs produced indicated the amount of [$^3$H]collagen IV or photo[$^3$H]collagen IV present on the surface of each piece.

The level of [$^3$H]collagen IV immobilized under each condition (Groups 1-6) was as follows: Group 1=725 ng/cm$^2$; Group 2=789 ng/cm$^2$; Group 3=81 ng/cm$^2$; Group 4=64 ng/cm$^2$; Group 5=331 ng/cm$^2$; and Group 6=715 ng/cm$^2$. It has been calculated that a monolayer of collagen IV on a surface would require approximately 500 ng/cm$^2$. The levels of [$^3$H]collagen IV immobilized in Groups 1 and 2 are sufficient to produce such a monolayer of collagen IV.

Therefore, it is apparent that tetra-BBE-PET (Groups 1 and 2) increases the level of [$^3$H]collagen IV immobilization over levels achieved by adsorption to an unmodified surface (Group 4), by adsorption to an illuminated bare surface (Group 3), or by illumination of [$^3$H]collagen IV without tetra-BBE-PET present (Group 5). The use of photo [$^3$H] collagen IV (Group 6) results in approximately equivalent loadings as seen in Group 1 and 2; however, the collagen IV was photoderivatized before use, thus the use of tetra-BBE-PET can eliminate the need for prior photoderivatization.

EXAMPLE 12

Immobilization of dDNA on Polystyrene Using Tetra-BBE-PET

Immobilization of double-stranded deoxyribonucleic acids ("dDNA") was accomplished by treatment of polystyrene microtiter plates with tetra-BBE-PET, followed by subsequent exposure of the modified surface with dDNA.

Radiolabeled DNA surface tenacity experiments were conducted to compare "raw" (i.e., untreated) polystyrene with the tetra-BBE-PET treated surface. To each of the 96 wells of standard medium-binding polystyrene microtiter strip plates (Costar, Inc.) was added 100 μl of 0.5 mg/ml tetra-BBE-PET in methanol. The plate was placed 25 cm (10 in) from a Dymax PC-2 lamp containing a 400 watt metal halide/mercury vapor bulb for 1.5 minutes (untreated control wells were not so treated). Each well was then rinsed three times with 300 μl of methanol and the plates allowed to air-dry.

A volume of 100 μl $^{32}$P-labelled Lambda DNA (50 kb dDNA bacteriophage, 35 pg DNA per well, 24 nCi per well) in phosphate buffered saline, pH 3.0, was added to each well of an untreated or (tetra-BBE-PET) treated polystyrene microtiter plate, incubated at ambient temperature for 1 hour, then illuminated for 4 minutes at a distance of 25 cm (10 in) from the Dymax lamp in a refrigerated cabinet (one untreated plate and one treated plate were not illuminated). The plates were then washed using one of two protocols to remove non-covalently absorbed dDNA:

Pre-hybridization solution—50% formamide, 5×Denhardt's solution (from 50×stock; 5 g Ficoll, 5 g PVP, 5 g BSA, 500 ml H$_2$O), 5×"SSPE" (from 20×stock: 174 g NaCl, 27.6 g NaH$_2$PO$_4$-H$_2$O, 7.4 g EDTA, 1 liter H$_2$O, pH 7.4), 0.1% SDS; 4×200 μl per well, followed by 1×300 μl for 60 minutes at 40° C., or Denaturing solution—0.4N NaOH, 0.25% SDS; 4×200 μl per well, followed by 1×300 μl for 15 minutes at 40° C.

Following the wash treatments, relative quantities of immobilized DNA were determined by breaking apart each of the 96 wells, dissolving each in 1.5 ml THF, adding 5 ml of scintillation cocktail (Aquasol-2, DuPont), and analyzing on a Packard 1900CA liquid scintillation analyzer. The results are tabulated below.

ence to raw polystyrene, and is thought to be accompanied by protein denaturation upon adsorption. (See, e.g., Jemmerson, R., "Antigenicity and Native Structure of Globular Proteins: Low Frequency of Peptide Reactive Antibodies", Proc. Nat. Acad. Sci. U.S.A., 84:9180, 1987; Stevens, F. J., "Considerations of the Interpretation of the Specificity of Monoclonal Antibodies Determined in Solid-Phase Immunoassays," in *Immunochemistry of Solid-Phase Immunoassay*, J. E. Butler, ed., CRC Press, 233, 1991; and Jemmerson, R., "Multiple Overlapping Epitopes in the Three Antigenic Regions of Horse Cytochrome c," *J. Immunol.* 138:213, 1987.)

Immobilization of Cyt c was accomplished by treating polystyrene microtiter plates with tetra-BBE-PET, followed by subsequent exposure of the modified surface with Cyt c.

Experiments were conducted using tritium-radiolabelled Cyt c to compare raw (i.e., untreated) polystyrene with tetra-BBE-PET treated surfaces. Standard medium-binding polystyrene microtiter strip plates (Costar, Inc.) were modified with 200 μl of 0.4 mg/ml tetra-BBE-PET in methanol in each of the 96 wells (untreated control wells were not coated). A volume of 150 μl was immediately removed from each well, and the plate was placed 25 cm (10 in) from a Dymax PC-2 lamp as described in Example 12 above for 2 minutes.

| WASH TREATMENT | AVERAGE DPM ± STANDARD DEVIATION OF IMMOBILIZED dDNA ON POLYSTYRENE MICROTITER PLATES | | | | |
|---|---|---|---|---|---|
| | RAW | RAW WITH ILLUMINATION | tetra-BBE-PET | tetra-BBE-PET WITH ILLUMINATION | % INCREASE IN DNA DUE TO tetra-BBE-PET |
| PRE-HYBRIDIZATION | 352 ± 38 | 7152 ± 1165 | 585 ± 43 | 9202 ± 1442 | 22% |
| DENATURING | 65 ± 20 | 1651 ± 89 | 195 ± 18 | 2969 ± 98 | 44% |

As can be seen, the immobilization of DNA using tetra-BBE-PET results in: a 26-fold increase over untreated polystyrene using the pre-hybridization solution wash method, and a 46-fold increase over untreated polystyrene using the denaturing wash method. Since this increase may be due in part to the photoillumination of DNA onto untreated polystyrene, the increase due only to covalent immobilization of DNA onto polystyrene using tetra-BBE-PET is indicated by a 22% increase in DNA using pre-hybridization wash and a 44% increase using a denaturing wash. These results clearly demonstrate that surface modification of polystyrene with tetra-BBE-PET followed by addition of dDNA and photoillumination is an effective method of immobilizing DNA to this support surface.

EXAMPLE 13

Immobilization of Horse Cytochrome c on PS using Tetra-BBE-PET

Horse Cytochrome c ("Cyt c") is a protein (MW approximately 12,400) that is commonly used as a model system for immunochemical studies. The structure of Cyt c has been studied extensively, including its protein sequence, tertiary structure, conformation of specific immunogenic epitopes, and structural changes that can occur when adsorbed to solid surfaces. This globular protein is known to demonstrate limited adher- The contents of each well were then immediately aspirated using an automated plate washer, and the plate was rinsed with 300 μl of IPA per well. The tetra-BBE-PET treated plates were air-dried in a 15% humidity-controlled environment before further testing. A volume of 100 μl $^3$H-labelled horse Cyt c at 4.2 μg/ml (0.34 μCi per weld in 0.05M carbonate-bicarbonate buffer, pH 9.6, was added to untreated or treated polystyrene, incubated on an environmental shaker set to rotate at 200 rpm at a temperature of 37° C. for 2 hours, then illuminated for 2 minutes at a distance of 25 cm (10 in) from a Dymax lamp using a 400 watt metal halide/mercury vapor bulb (one untreated plate and one treated plate were not illuminated).

The plates were then aspirated, and washed as follows: four washes, each with 200 μl /well, of 50 mM Tris, 150 mM NaCl, and 0.05% (v/v) Tween-20, pH 7.5 ("TNT"), followed by an incubation with 200 μl TNT per well on an environmental shaker rotating at 200 rpm at 37° C. for 2 hours, and three final washes, each with 300 μl TNT. Following the final wash, the polystyrene wells were broken apart, dissolved in 1.5 ml THF, and counted by liquid scintillation spectroscopy as described in Example 12 above, using 5 ml scintillation fluor. The resulting disintegrations per minute ("dpm") were translated to average ng protein per well. The results of this experiment were:

| PLATE TREATMENT | CYTOCHROME c IMMOBILIZATION TO TETRA-BBE-PET TREATED POLYSTYRENE | |
| --- | --- | --- |
| | NOT ILLUMINATED AFTER CYT c ADDITION | ILLUMINATED AFTER CYT c ADDITION |
| RAW POLYSTYRENE | 7.15 ± 2.58 | 79.67 ± 16.37 |
| tetra-BBE-PET POLYSTYRENE | 126.38 ± 12.4 | 173.33 ± 5.63 |

As can be seen above, surface modification by covalent bonding of Cyt c to polystyrene via this photoreagent resulted in: a 24-fold increase relative to adsorption to raw polystyrene; a 2-fold increase relative to UV light-potentiated adsorption to raw polystyrene, and, a 1.4-fold increase relative to tetra-BBE-PET treated polystyrene without photoimmobilization (illumination) of the Cyt c to the surface. These results clearly demonstrate that the tetra-BBE-PET treated polystyrene surface is useful for covalent immobilization of proteins to this solid support matrix.

EXAMPLE 14

Surface Modification of Polyethylmethacrylate (PMMA) by Sequential Application of tetra-BBA-PET and Polyvinlypyrolidone (PVP)

A clear PMMA coupon (Rohm & Haas), 4 cm (1.57 in.)×2 cm (0.78 in.)×2 mm (0.08 in.) was wiped with an IPA soaked tissue, after which one-half of the coupon was brushed with a 0.08 mg/ml solution of tetra-BBA-PET in methanol. After the coating had air-dried for 5 minutes under normal laboratory conditions, the entire coupon was illuminated for 30 seconds, 150 mm (6 in.) from a 100 watt short arc mercury vapor bulb. After a rinse with excess IPA to remove unbound tetra-BBA-PET, the entire coupon was then brush coated with 10 mg/ml of PVP (160,000 molecular weight no. ave. value, GAF Chemical Corp.) in DI water. After the PVP had air-dried (approximately 5 minutes), the coupon was again illuminated for 30 seconds, 150 mm (6 inches) from the same light source and in the same manner. The coupon was then rubbed extensively between fingers (approximately 1 minute) under a flow of DI water to check the durability of the PVP coating.

After this rinse, the half coated with tetra-BBA-PET remained noticeably more wettable and lubricious to the touch than the half of the coupon that was coated with PVP alone. The presence of the bound PVP on the tetra-BBA-PET coated half was verified by staining with a 0.35% solution of Congo Red (Sigma) in DI water.

We claim:

1. A restrained, multifunctional reagent selected from the group consisting of the tetrakis (4-benzoylbenzyl ether) and the tetrakis (4-benzoylbenzoate ester) of pentaerthyritol.

2. A restrained, multifunctional reagent according to claim 1 wherein the reagent comprises the tetrakis (4-benzoylbenzyl ether) of pentaerythritol.

3. A restrained, multifunctional reagent according to claim 2 wherein a plurality of the 4-benzoylbenzyl ether groups have been activated in order to attach them to a surface.

4. A restrained, multifunctional reagent according to claim 2 wherein a plurality of the 4-benzoylbenzyl ether groups have been activated in order to attach them to a target molecule.

5. A restrained, multifunctional reagent according to claim 2 wherein a plurality of the 4-benzoylbenzyl ether groups have been activated in order to attach them to a target molecule and a different plurality have been activated in order to attach them to a surface.

6. A restrained, multifunctional reagent according to claim 4 wherein the target molecule is selected from the group consisting of synthetic polymers, carbohydrates, proteins, lipids, nucleic acids, drugs, vitamins, and co-factors.

7. A restrained, multifunctional reagent according to claim 3 wherein the surface provides abstractable hydrogens suitable for covalent bonding with the activated group.

8. A restrained, multifunctional reagent according to claim 7 wherein the surface is provided by a support selected from the group consisting of polyolefins, polystyrenes, poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, cellulose derivatives, silicones, and rubber-like plastics.

9. A restrained, multifunctional reagent according to claim 1 wherein the reagent comprises the tetrakis (4-benzoylbenzoate ester) of pentaerythritol.

10. A restrained, multifunctional reagent according to claim 9 wherein a plurality of the 4-benzoylbenzoate ester groups have been activated in order to attach them to a surface.

11. A restrained, multifunctional reagent according to claim 9 wherein a plurality of the 4-benzoylbenzoate ester groups have been activated in order to attach them to a target molecule.

12. A restrained, multifunctional reagent according to claim 9 wherein a plurality of the 4-benzoylbenzoate ester groups have been activated in order to attach them to a target molecule and a different plurality have been activated in order to attach them to a surface.

13. A restrained, multifunctional reagent according to claim 11 wherein the target molecule is selected from the group consisting of synthetic polymers, carbohydrates, proteins, lipids, nucleic acids, drugs, vitamins, and cofactors.

14. A restrained, multifunctional reagent according to claim 10 wherein the surface provides abstractable hydrogens suitable for covalent bonding with the activated group.

15. A restrained, multifunctional reagent according to claim 14 wherein the surface is provided by a support selected from the group consisting of polyolefins, polystyrenes, poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, cellulose derivatives, silicones, and rubber-like plastics.

16. A restrained, multifunctional reagent comprising an acylated derivative of tetraphenylmethane.

17. A restrained, multifunctional reagent according to claim 16 wherein the reagent a plurality of the acyl groups have been activated in order to attach them to a surface.

18. A restrained, multifunctional reagent according to claim 16 wherein a plurality of the acyl groups have been activated in order to attach them to a target molecule.

19. A restrained, multifunctional reagent according to claim 16 wherein a plurality of the acyl groups have been activated in order to attach them to a target molecule and a different plurality have been activated in order to attach them to a surface.

20. A restrained, multifunctional reagent according to claim 19 wherein the target molecule is selected from the group consisting of synthetic polymers, carbohydrates, proteins, lipids, nucleic acids, drugs, vitamins, and cofactors, and the surface is provided by a support selected from the group consisting of polyolefins, polystyrenes, poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, cellulose derivatives, silicones, and rubber-like plastics.

* * * * *